US006287749B1

(12) United States Patent
Nagarajan et al.

(10) Patent No.: US 6,287,749 B1
(45) Date of Patent: Sep. 11, 2001

(54) BIRADICAL PHOTOINITIATORS AND PHOTOPOLYMERIZABLE COMPOSITIONS

(75) Inventors: Rajamani Nagarajan, Ocean Springs, MS (US); Joseph Stanton Bowers, Jr., Mobile, AL (US); Charles E. Hoyle, Hattiesburg, MS (US); E. Sonny Jönsson, Stockholm (SE); John R. I. Eubanks, Ocean Springs, MS (US)

(73) Assignees: First Chemical Corporation, Pascagoula; Univ. of Southern Mississippi, Hattiesburg, both of MS (US)

( * ) Notice: Subject to any disclaimer, the term of this patent is extended or adjusted under 35 U.S.C. 154(b) by 0 days.

(21) Appl. No.: 09/072,080

(22) Filed: May 4, 1998

Related U.S. Application Data

(60) Provisional application No. 60/045,621, filed on May 5, 1997.

(51) Int. Cl.⁷ ............................. G03F 7/027; C08K 2/46; C07C 49/115
(52) U.S. Cl. .................. 430/281.1; 430/916; 430/923; 522/68; 568/328; 568/330; 568/375
(58) Field of Search .................... 568/328, 330, 568/375; 522/68, 30, 281.1; 430/916, 923, 270.1

(56) References Cited

U.S. PATENT DOCUMENTS

| 3,801,327 | * | 4/1974 | Moreau | 96/115 R |
|---|---|---|---|---|
| 4,308,400 | * | 12/1981 | Felder et al. | 568/336 |
| 4,510,321 | * | 4/1985 | Masilamani et al. | 562/421 |
| 5,554,641 | * | 9/1996 | Horwell et al. | 514/415 |
| 5,756,790 | * | 5/1998 | Mukaiyama et al. | 556/32 |
| 5,773,486 | * | 6/1998 | Chandross et al. | 522/33 |
| 5,780,465 | * | 7/1998 | Markley et al. | 514/224.2 |

FOREIGN PATENT DOCUMENTS

| 0 373 662 A | 6/1990 | (EP) . |
|---|---|---|
| 2 161 482 A | 1/1986 | (GB) . |
| 8-310981 | * 11/1996 | (JP) . |

OTHER PUBLICATIONS

Shtelzer, S. et al. J. Hetero. Chem. 1984 21 (6), 1593–95.*
Tsonetsugu, J. et al J. Chem. Soc. Perkin Trans. I 1986, 11 1965–1973.*
Davis, F.A., et al. Tettahedron Lett. 1988 29 (35) 4365–4368.*
Galasso, V. J. Chem. Soc. Perkin Trans. II, 1976, 5, 574–578.*
Popp, F.D., J. Heter. Chem. 1974 11 (1), 79–82.*
Paul, T. J. Org. Chem. 1996 61, 6835–6848.*
Hark, R.R., Tetrahedron Lett. 35(42) 7719–7722, 1994.*
March., J. Advanced Organic Chemistry, 4th Ed. Wiley, NY. 1992, pp. 242–244, 1046–1047.*
Turro, N. J. Molecular Photochemistry, W.A Benjamin, NY 1965, pp. 224–226.*
Alger, M.S. Polymer Science Dictionary, Elsevier N.Y. 1989, pp. 174–175.*
Database WPI Jan. 8, 1990, Derwent Publications Ltd., London, GB;; AN 3944, XP002074689, "Photopolymerizable Composition and Recording Medium Using Same," & JP 01 253 732 A (Canon Inc.), Oct. 11, 1989.
M.J. Climent, "Photolysis of Cyclic Enol Esters in the Presence or Absence of a Single Electron Transfer Photosensitizer," *Tetrahedron*, vol. 47, No. 44, 1991, pp. 9289–9296, XP002074687.
D.S. Tarbell, "Mannich Bases and Other Compounds Derived from Benzsuberone," *Journal of the American Chemical Society*, vol. 74, Dec. 20, 1952, pp. 6263–6266, XP002074688.

\* cited by examiner

*Primary Examiner*—Rosemary E. Ashton
(74) *Attorney, Agent, or Firm*—Alston & Bird LLP

(57) ABSTRACT

Biradical initiators and methods using the same are disclosed. Polymerization of compositions which include the compounds of the invention may be activated by irradiating the composition with radiation.

20 Claims, 2 Drawing Sheets

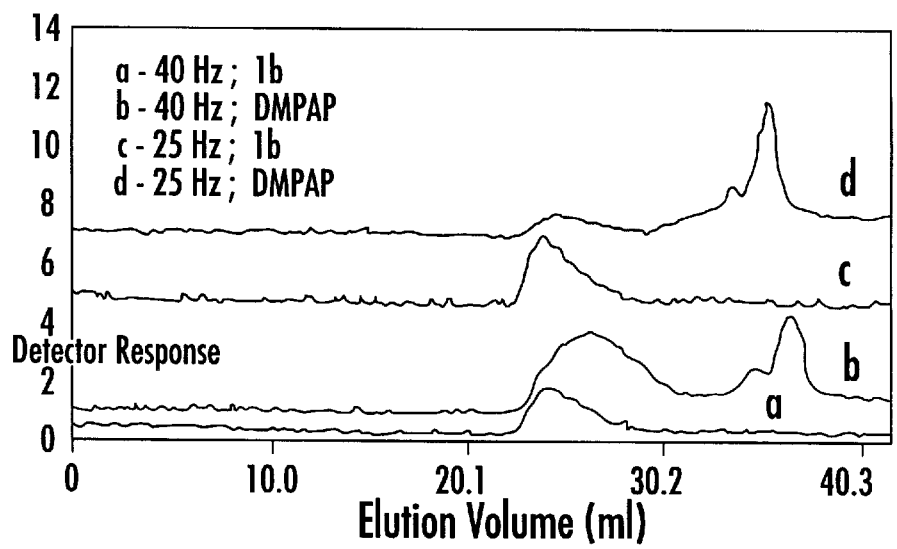
FIG. 3. SEC Traces of Poly(methyl methacrylate) formed by the LIP of Methyl Methacrylate at Different Repetition Rates
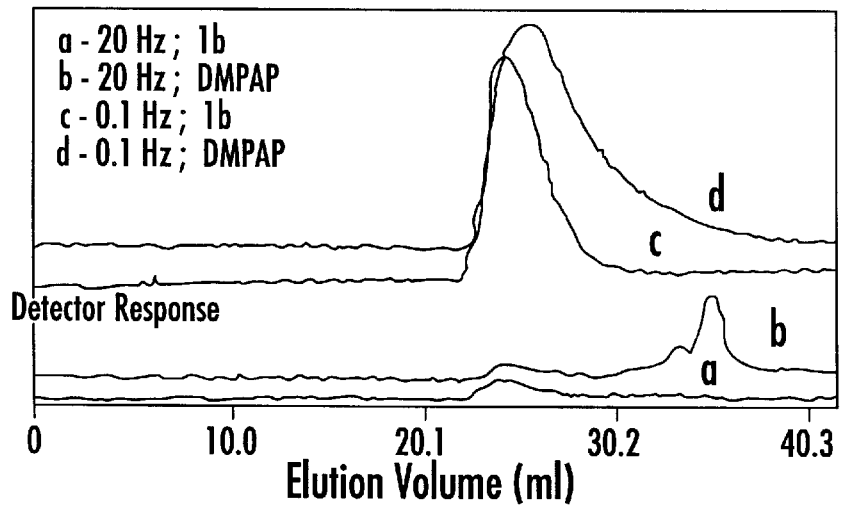
FIG. 4. SEC Traces of Poly(methyl methacrylate) formed by the LIP of Methyl Methacrylate at Different Repetition Rates

BIRADICAL PHOTOINITIATORS AND PHOTOPOLYMERIZABLE COMPOSITIONS

CROSS-REFERENCE TO RELATED APPLICATION

This application is related to commonly owned copending Provisional Application Serial No. 60/045,621, filed May 5, 1997 abandoned and claims the benefit of its filing date under 35 USC Section 119(e).

FIELD OF THE INVENTION

This invention relates to compounds useful for initiating polymerization of ethylenically unsaturated compounds, and in particular to compounds useful for initiating polymerization upon exposure to radiation and to methods for using the same.

BACKGROUND OF THE INVENTION

Ethylenically unsaturated compounds, such as acrylate derivatives, can be polymerized by exposure to actinic radiation, typically ultraviolet light, in the presence of a photoinitiating system. Photoinitiating systems include a photoinitiator, which is a compound capable of forming mono-radicals (molecular fragments having one unpaired electron) upon exposure to radiation. The mono-radicals can be formed via various mechanisms, such as α-cleavage or hydrogen abstraction, when the photoinitiator is exposed to radiation. An example of a conventional mono-racial formed by an α-cleavage mechanism is illustrated below:

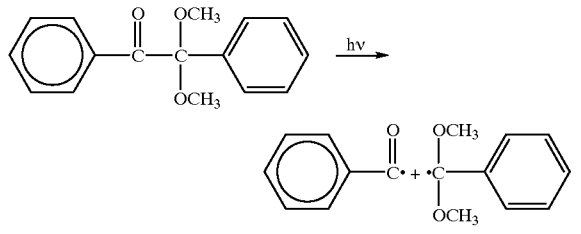

The resultant mono-radicals can initiate polymerization by reacting with the desired compound to be polymerized to form active growing polymer chains.

Numerous mono-radical forming photoinitiators are commercially available. Despite their advantages, conventional mono-radical forming photoinitiators can suffer various disadvantages. For example, during free racial polymerization, the rate constant for termination ($k_t$) can be several orders of magnitude larger than the rate constant for propagation ($k_p$) ("Principles of Polymerization," G. Odian, McGraw-Hill, N.Y., 1970, page 171–2), particularly during the early stages of polymerization when the viscosity of the polymerization medium can be low. Premature termination can occur, for example, if the active radical polymer chain couples with another polymer chain or with an initiator radical. Premature termination can in turn adversely impact cure rates, molecular weight and molecular weight distribution of the resultant product, and the like.

Still further, cured articles formed using mono-radical photoinitiators can include residual fragment molecules. Residuals present in the cured article can create offensive odors and can degrade the physical properties of the article, such as light fastness, coloration, and resistance to oxidative degradation. In addition, residuals can be extracted or leach out of the cured article or migrate to the surface of the article.

SUMMARY OF THE INVENTION

The present invention is directed to compounds useful in radiation curing of photopolymerizable compounds. In contrast to conventional photoinitiators, which form monoradicals with just one active site, the compounds of the invention are capable of forming biradicals, that is, at least two molecular fragments having one unpaired electron, upon exposure to radiation. Because at least two active sites can be formed, during free racial polymerization, the rate constant for termination can be reduced because various termination mechanisms observed in conventional mono-radical systems can eliminated or minimized. For example, attack of another propagating radical can lead to formation of a macroradical, which can further initiate polymerization, instead of resulting in termination as in the case with conventional mono-radical initiators.

As a result, the compounds can be used to form polymers with increased molecular weights and/or narrower molecular weight distributions. Still further, the compounds can provide increased polymerization rates as compared to convention mono-radical photoinitiators. In addition, articles prepared using the compounds of the invention can have minimal or no residual fragment molecules, and thus can exhibit reduced odors, improved physical properties, and reduced amounts of extractable and migratable compounds. The compounds of the invention are also currently believed to provide "dark cure," that is, continued cure after the radiation source is removed.

The compounds of the invention have the general formula (I)

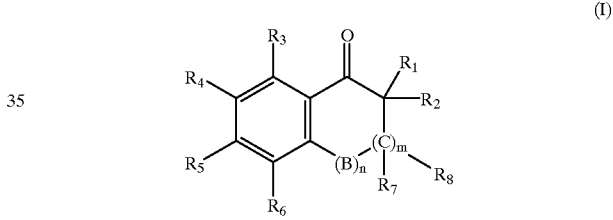

wherein:

$R_1$ and $R_2$ are each independently selected from the group consisting of lower alkoxy, lower alkyl, nitrile, aryl, hydroxy, and oxygen, with the proviso that if either $R_1$ or $R_2$ is oxygen, the other of $R_1$ or $R_2$ does not exist;

$R_3$, $R_4$, $R_5$, $R_6$, $R_7$ and $R_8$ are each independently selected from the group consisting of hydrogen, lower alkoxy, lower alkyl, nitrile, aryl, and halogen, or $R_7$ and $R_8$ together can represent C2 to C10 alkylene, oxaalkylene, or azaalkylene, or when B is not present, $R_6$ and $R_7$ together with the carbon atoms to which they are attached can form a fused aromatic ring, or when B is C, $R_7$ and B together with the carbon atom to which $R_7$ is attached can form a fused aromatic ring;

B is selected from the group consisting of C, C=O, N—$R_{11}$, O, S, and C($R_9$) ($R_{10}$), wherein $R_9$ and $R_{10}$ are each independently selected from the group consisting of hydrogen, lower alkoxy, lower alkyl, nitrile, aryl, and halogen; $R_{11}$ is selected from the group consisting of hydrogen, lower alkyl, aryl, and —C(O)$R_{12}$; and $R_{12}$ is selected from the group consisting of lower alkyl, lower alkoxy, aryl, and aryloxy;

m is 0, 1 or 2; and n is 0 or 1.

The present invention also provides photopolymerizable compositions which include the compounds of Formula (I)

above as a component thereof, and methods for the use of the compounds of Formula (I) in photopolymerization systems.

BRIEF DESCRIPTION OF THE DRAWINGS

Some of the features and advantages of the invention having been described, others will become apparent from the detailed description which follows, and from the accompanying drawings, in which:

FIG. 3 is a SEC produced from LIP of MMA using DMPAP and a compound in accordance with the invention at a repetition rate of 25 and 40 Hz; and FIG. 4 is a SEC produced from LIP of MMA using DMPAP and a compound in accordance with the invention at a repetition rate of 0.1 and 20 Hz.

DETAILED DESCRIPTION OF THE INVENTION

Figure 1:
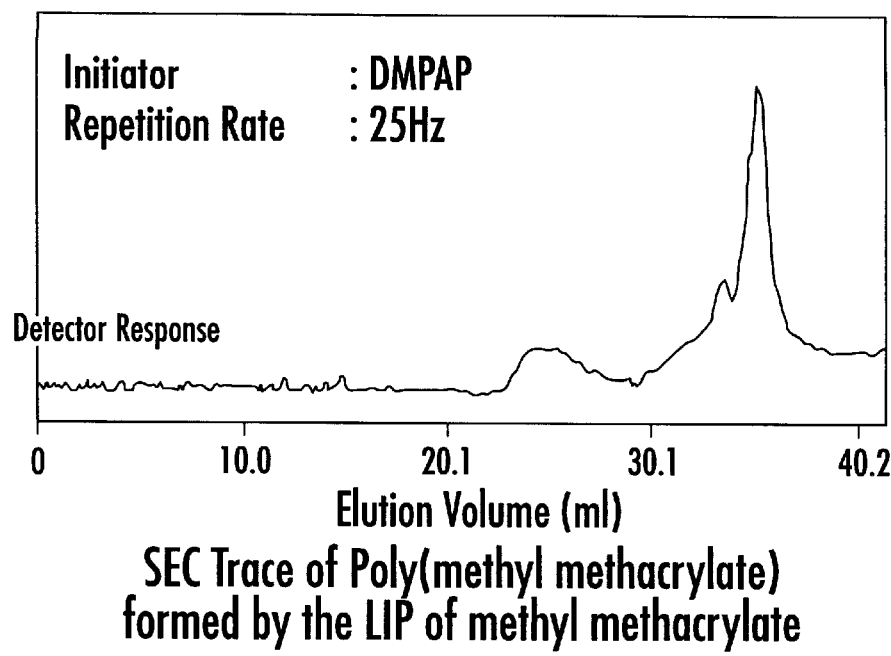
FIG. 1 is a size exclusion chromatograph (SEC) produced from laser initiated polymerization (LIP) of methyl methacrylate (MMA) using a conventional initiator 2:2 dimethoxy 2-phenyl acetophenone (DMPAP) at a repetition rate of 25 Hz.

The compounds of the invention include compounds according to Formula (I) below:

(I)

wherein:
R$_1$ and R$_2$ are each independently selected from the group consisting of lower alkoxy, lower alkyl, nitrile, aryl, hydroxy, and oxygen, with the proviso that if either R$_1$ or R$_2$ is oxygen, the other of R$_1$ or R$_2$ does not exist;

R$_3$, R$_4$, R$_5$, R$_6$, R$_7$ and R$_8$ are each independently selected from the group consisting of hydrogen, lower alkoxy, lower alkyl, nitrile, aryl, and halogen, or R$_7$ and R$_8$ together can represent C2 to C10 alkylene, oxaalkylene, or azaalkylene, or when B is not present, R$_6$ and R$_7$ together with the carbon atoms to which they are attached can form a fused aromatic ring, or when B is C, R$_7$ and B together with the carbon atom to which R$_7$ is attached can form a fused aromatic ring;

B is selected from the group consisting of C, C=O, N—R$_{11}$, O, S, and —C(R$_9$)(R$_{10}$), wherein R$_9$ and R$_{10}$ are each independently selected from the group consisting of hydrogen, lower alkoxy, lower alkyl, nitrile, aryl, and halogen; R$_{11}$ is selected from the group consisting of hydrogen, lower alkyl, aryl, and —C(O)R$_{12}$; and R$_{12}$ is selected from the group consisting of lower alkyl, lower alkoxy, aryl, and aryloxy;

m is 0, 1 or 2; and n is 0 or 1.

In one preferred embodiment of the invention, R$_1$ and R$_2$ are each lower alkoxy, more preferably C1 to C4 alkoxy, and most preferably methoxy or ethoxy; R$_3$, R$_4$, R$_5$, R$_6$, R$_7$ and R$_8$ are each hydrogen; m is 1; B is C; and n is 1.

In another preferred embodiment of the invention, R$_1$ and R$_2$ are each lower alkoxy, more preferably C1 to C4 alkoxy, and most preferably methoxy or ethoxy; R$_3$, R$_4$, R$_5$, R$_6$, R$_7$ and R$_8$ are each hydrogen; m is 1; and n is 0.

In yet another preferred embodiment of the invention, R$_1$ and R$_2$ are each lower alkoxy, more preferably C1 to C4 alkoxy, and most preferably methoxy or ethoxy; R$_3$, R$_4$, R$_5$, and R$_6$ are each hydrogen; m is 1; B is C and n is 1; and R$_7$ and B together with the carbon atom to which R$_7$ is attached is phenyl.

As used herein, the term "lower alkyl" refers to C1 to C10 straight chain or branched alkyl, such as methyl, ethyl, propyl, isopropyl, butyl, tert-butyl, sec-butyl, pentyl, hexyl, and the like. The term "aryl" refers to C6 to C10 cyclic aromatic groups, such as phenyl, naphthyl, and the like, optionally substituted with lower alkyl. The term "lower alkoxy" refers to C1 to C10 straight chain or branched alkoxy. When R$_8$ and R$_2$ together are C2 to C10 alkylene, oxaalkylene, or azaalkylene, R$_8$ and R$_2$ can in this case together with the carbon atom to which they are attached form cyclopropane, cyclobutane, cyclopentane, cyclohexane, cycloheptane, tetrahydrofuran, tetrahydropyran, pyrrolidine, piperidine, and the like.

Exemplary compounds of the invention include, but are not limited to:

(Ia)

(Ib)

(Ic)

(Id)

(Ie)

-continued

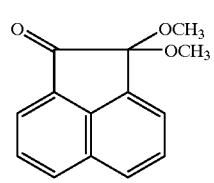
(If)

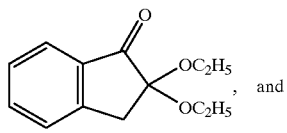
, and
(Ig)

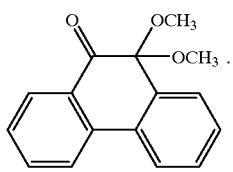
(Ih)

Generally, the compounds of Formula (I) can be prepared using techniques known in the art, with slight modifications as noted herein and as will be appreciated by the skilled artisan. For example, diketones ($R_1$ is =O) can be prepared by oxidizing a monoketone with alkyl nitrite. Ketals ($R_1$ and $R_2$ are each alkoxy) can be prepared by the methods disclosed in U.S. Pat. No. 4,967,010, the entire disclosure of which is incorporated herein by reference, by reacting a diketone with trialkylorthoformate or dialkyl sulfite. Nitriles ($R_1$ is CN) can be prepared by displacing halogen, especially bromide, from alpha-halo substituted ketones such as 2-bromobenzocycloheptan-1-one. Hydroxy compounds can be prepared by catalytic oxidation of alpha-alkyl substituted ketones.

The present invention also provides photopolymerizable compositions which include a compound of Formula (I) as a component thereof as a photoinitiator which is capable of forming a radical with at least two active sites upon exposure to radiation. As used herein, and as will be appreciated by the skilled artisan, the term photopolymerizable composition refers to compositions which harden or cure upon exposure to radiation.

Generally the compositions of the invention include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of radiation (ultraviolet or UV radiation, or radiation outside the UV spectrum). As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitriles. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, vinyl and vinylidene esters, ethers, and ketones, butadiene, vinyl aromatics, i.e., styrene, alkyl styrenes, halostyrenes, divinyl benzenes, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

The photopolymerizable compound can be present in the compositions of the invention in amounts between about 30 and about 99 percent by weight based on the total weight of the composition, preferably between about 50 and about 99 percent by weight.

The compounds of Formula (I), singly or as a mixture thereof, are useful as photopolymerization initiators. In this aspect of the invention, the compounds of Formula (I) are present in the photopolymerizable composition in an amount sufficient to initiate polymerization thereof upon exposure to radiation. The composition can include about 0.1 to about 15 percent by weight photoinitiator, based on the total weight of the photopolymerizable compounds.

Although not wishing to be bound by any theory of the invention, it is currently believed that the compounds of the invention are capable of forming biradical compounds upon exposure to radiation and thus can be useful for initiating photopolymerization of radiation curable compounds. It is currently believed that the compounds produce a biradical compound via an α-cleavage mechanism to provide at least two active sites as represented schematically below:

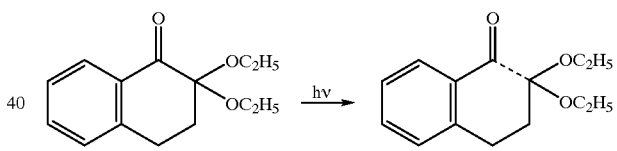

The exemplary reaction shown above illustrates that the initiating radical can attack two monomer molecules simultaneously, and further the attack of a propagation racial can produce another macroradical, instead of causing termination. In view of this proposed mechanisms, it is currently believed that the rate of reaction can be higher than that for a conventional initiator that produces a mono-racial.

The photopolymerizable compositions of the invention may also contain other conventional agents, such as polymerization inhibitors, fillers, ultraviolet absorbers and organic peroxides. It can also be advantageous to also include as a component of the compositions of the invention a coinitiator or synergist, that is, a molecule which serves as a hydrogen atom donor. Coinitiators or synergists are known in the art, and are typically alcohols, tertiary amines or ethers which have available hydrogens attached to a carbon adjacent to a heteroatom. Such coinitiators are typically present in an amount between about 0.2 and about 25 percent by weight based on the total weight of the composition. Suitable compounds include, but are not limited to, triethanolamine, methyl-diethanolamine, ethyldiethanolamine and esters of dimethylamino benzoic acid. Other known coinitiators or accelerators can also be used. These compounds behave as coinitiators or accelerators for the primary photoinitiators and can increase the efficiency and speed of the polymerization process.

The photopolymerizable compositions can be applied or deposited on a surface of a substrate using conventional techniques and apparatus. The composition can be applied as a substantially continuous film. Alternatively, the composition can be applied in a discontinuous pattern. The thickness of the deposited composition can vary, depending upon the desired thickness of the resultant cured product.

Typically, the substrate is coated with the uncured photopolymerizable composition and passed under a ultraviolet providing light beam by a conveyer moving at predetermined speeds. The substrate to be coated can be, for example, metal, wood, mineral, glass, paper, plastic, fabric, ceramic, and the like.

The active energy beams used in accordance with the present invention may be visible light or ultraviolet light or may contain in their spectra both visible and ultraviolet light. The polymerization may be activated by irradiating the composition with ultraviolet light using any of the techniques known in the art for providing ultraviolet radiation, i.e., in the range of 200 nm and 450 nm ultraviolet radiation, or by irradiating the composition with radiation outside of the ultraviolet spectrum. The radiation may be natural or artificial, monochromatic or polychromatic, incoherent or coherent and should be sufficiently intense to activate the photoinitiators of the invention and thus the polymerization. Conventional radiation sources include fluorescent lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention.

The compositions are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The present invention will be further illustrated by the following non-limiting examples.

EXAMPLE 1

Synthesis of 2,2-Diethoxy-1-tetralone 2,2-Diethoxy-1-tetralone (compound Ib) was prepared by charging 48.9 g of 1-tetralone, 105 g of absolute ethanol, 5.2 g of gaseous hydrogen chloride to a reactor flask. To another flask (feeder flask) was added 62.6 g of ethyl nitrite. The feeder flask was connected to the reaction flask by a hose ending with a gas dispersion tube which would allow subsurface addition of the ethyl nitrite. The feeder flask was maintained at room temperature to facilitate ethyl nitrite evaporation. The ethyl nitrite was added to the reaction, with stirring, over about 60 minutes at a reaction temperature of 40–42° C. When the addition was complete, the mixture was neutralized to pH 8 and then ethanol was vacuum stripped on a rotary evaporator. The residue was held for 2 hours at about 50° C. to complete the saponification. The product was extracted into hexane and the hexane removed under vacuum. The residue was distilled under vacuum (0.2–0.5 mm Hg) to give 1.9 g of product. NMR, IR and MS were consistent with the proposed structure.

EXAMPLE 2

Synthesis of Methyl Ketal of Acenaphthalene Quinone

The methyl ketal of acenaphthalene quinone (compound If) was prepared by slurrying about 2 g of acenaphthalene quinone in methanol. About 5 ml of thionyl chloride ($SOCl_2$) was added slowly allowing the temperature to go to reflux and holding it there during the addition, The addition took about 15 minutes. The reaction mixture was held for another 15 minutes and then quenched into 300 ml of 10% NaOH. The crude product crystallized and was filtered and recrystallized from methanol. The recovered product weighed 2.5 g, had an off white appearance and a melting point of 123–124° C.

EXAMPLE 3

Synthesis of Methyl Ketal of Phenanthrene Quinone

The methyl ketal of phenanthrene quinone (compound Ih) was prepared using the procedure described above in Example 2, except substituting phenanthrene quinone for acenaphthalene quinone. The isolated product weighed 1.3 g, had a light brown appearance and a melting point of 103–104° C.

EXAMPLE 4

Synthesis of 2,2-Dioxoindanone 2,2-dioxoindanone (compound Ic) was prepared by charging 13.21 g of 1-indanone, 39.7 g of absolute ethanol, and 3.10 g of gaseous hydrogen chloride to a reactor flask. To another flask (feeder flask) was added 20.2 g of ethyl nitrite. The feeder flask was connected to the reaction flask as described in Example 1. The ethyl nitrite was slowly evaporated and fed to the reactor as a gas over about 40 minutes. The reaction mixture was cooled to room temperature and filtered. The precipitate was recrystallized from ethanol. Dark yellow crystals were obtained. Weight of the dry product was 6.096 g. The product had a melting point of 203–204° C. The product was analyzed by $^1H$ and $^{13}C$-NMR and identified as 1,2-dioxoindane.

EXAMPLE 5

Synthesis of 2-Cyanobenzocycloheptan-1-one 2-bromobenzocycloheptan-1-one was prepared by dissolving benzocycloheptan-1-one (25.15 g, 0.157 mol) in acetic acid (200 mL, 99.8%) in a 500 mL three neck flask. Bromine (25.15 g, 0.157 mol) and acetic acid (10 mL) were placed in a dropping funnel. The bromine was slowly added dropwise to the flask over 4 hours at room temperature. The reactor was kept under a static blanket of nitrogen throughout. Then the reaction was held at room temperature for an additional four hours. The reaction mixture was washed with water (200 mL×2) and dried over sodium sulfate. A brown colored liquid (30.2 g) as a crude product was obtained after filtration from the sodium sulfate. The purity of the product was 96.4% by GC (area %).

2-cyanobenzocycloheptan-1-one (compound Ia) was prepared by dissolving 2-bromobenzocycloheptan-1-one (30.2 g, 0.126 mol) in toluene (150 mL) in a 500 mL round bottom flask equipped with a condenser. NaCN (18.6g, 0.38 mol), water (50 g), and dibenzo-18-crown-6 (0.5 g) were added to the flask. The reaction mixture was stirred vigorously at 90° C. under a static blanket of nitrogen for 15 hours. The reaction mixture was cooled and washed three times with water (70 mL×2+100 mL). The toluene solution was dried over sodium sulfate and filtered. The solvent was evaporated under reduced pressure. The residue was distilled under vacuum to give a yellow liquid (21.1 g, b.p. 158–162° C. at 17 mm Hg). The purity of the liquid was 96% by GC.

EXAMPLE 6

Synthesis of 2-Hydroxy-2-methyl-benzocyclohexan-1-one

2-Hydroxy-2-methyl-benzocyclohexan-1-one (compound Id) was prepared by dissolving 2-methyl-benzocyclohexan-1-one (19.7 g, 0.123 mol) in toluene (750 mL) in a 2000 mL three neck flask. Triethyl phosphite (98%, 25 mL, 0.2 mol) and N-[4-(trifluoromethyl)benzyl]-cinchoninium bromide (CPTC, 3.3 g, 6.25 mmol, 5 mol %) and 50% aqueous sodium hydroxide (375 mL) were added into the flask. A Pasteur pipet was installed in one neck and immersed in the solution to serve as an inlet for oxygen. One of the other necks was attached to a condenser which was topped with an outlet opening to air. A mechanical stirrer was used to keep the two phase solution stirring vigorously. Molecular oxygen was bubbled through the reaction mixture and the solution was kept stirring for 24 hours at room temperature. After the reaction, water (400 mL) was added to the mixture. The water layer and toluene layer were separated using a separatory funnel. The aqueous layer was extracted with benzene (100 mL×3). The benzene portion and the toluene portion were combined. The organic layer was washed with 10% hydrochloric acid (350 mL), water and finally with saturated aqueous sodium chloride. The organic layer was dried over sodium sulfate. The organic solvent was removed by a rotary evaporator to give a yellow liquid. The yellow liquid was purified by vacuum distillation. Two fractions corresponding to a boiling range of 110–113° C. at 17 mm Hg (triethyl phosphite) and 135–140° C. at 17 mm Hg (the desired compound) were collected separately. The fraction containing 2-hydroxy-2-methyl-benzocyclohexan-1-one (14.5 g) was obtained in 67% isolated yield. The purity of the product was 100% by GC.

EXAMPLE 7

Polymerization of Monomers and Oliaomers

A clear coat formulation was prepared using monomers and oligomers supplied by UCB Radcure. The formulation included 58 weight percent Ebecryl 80 (a polyester polyol derivative); 29 weight percent tripropylene glycol diacrylate; and 13 weight percent OTA-480 (a glyceryl propoxy triacrylate).

To the above clear coat formulation, 4 weight percent of the biradical initiators (Ia)–(Ih) above was added and dissolved by agitation in an ultrasonic bath. 2 mil films of the above solutions were cast on paper panels and cured using a Fusion UV curing unit under the following conditions: the lamp source was a Fusion Systems "D" bulb; power was 600 W/in.; and belt Speed was 85 ft./min.

EXAMPLE 8

Evaluation of Polymerization Mechanism

To demonstrate that the compounds of the invention cure via a biradical mechanism, laser initiated polymerization (LIP) was used to produce polymers using a conventional initiator 2:2 dimethoxy 2-phenyl acetophenone (DMPAP) and compounds Ia, Ib, Id and Ih. Previous studies have indicated that the repetition rate of laser pulses influences the molecular weight of the polymer produced. C. E. Hoyle, et al., Macromolecules 1989. As the repetition rate is increased, molecular weight decreases. Id. It is believed that as a new laser pulse is delivered to the system, new initiating radicals are produced from the photoinitiator and the newly produced radicals intercept the propagating radicals in addition to initiating polymerization of new monomer molecules. As a result, the number of termination reactions increases, leading to an overall reduction in the molecular weight of the polymer produced.

It is theorized that if the compounds of the invention initiate polymerization by a biradical mechanism, then the resulting polymer can have a higher molecular weight as compared to polymers produced using a conventional initiator that produces mono-radicals. Accordingly, the molecular weight of the resultant polymers was analyzed.

To conduct the polymerization, the initiators were dissolved in methyl methacrylate (MMA) and the concentrations used were such that their optical density at 358 nm was 0.5. Aliquots of 3 ml solutions were taken in a 1 cm quartz cell and 200 pulses delivered to each solution. Each sample was purged with nitrogen for 2 minutes prior to exposure to the laser. The laser used was a Questek Model Series 2000 excimer with a xenon-fluorine fill gas mixture.

A size exclusion chromatographic (SEC) system was assembled with a Waters 6000 solvent delivery pump, a model 7010 rheodyne injector with a 50 μl injection loop, a Waters 410 differential refractometer and four Waters styrgel HR columns ($10^2$, $10^3$, $10^4$, and $10^5$) enclosed in a Waters column heater. The temperature of the columns was maintained at 35° C. The mobile phase was tetrahydrofuran and the flow rate was 1 ml/min. The SEC system was calibrated using narrow molecular weight poly(methyl methacrylate) standards supplied by Polymer Laboratories, U.K.

The SEC chromatogram obtained for the polymer produced from the LIP of MMA using DMPAP at a repetition rate of 25 Hz is shown in FIG. 1. The splitting of the low molecular weight peak is the result of premature termination of the propagating radicals at high repetition rates, as reported above. It is expected that the shape of the low molecular weight peak will be different for initiators that initiate polymerization by a biradical mechanism, i.e., as the attack of the new initiator radicals would not cause termination of the propagating radicals, the splitting observed for the low molecular weight peak should disappear and shift towards the higher molecular weight region.

Figure 2:
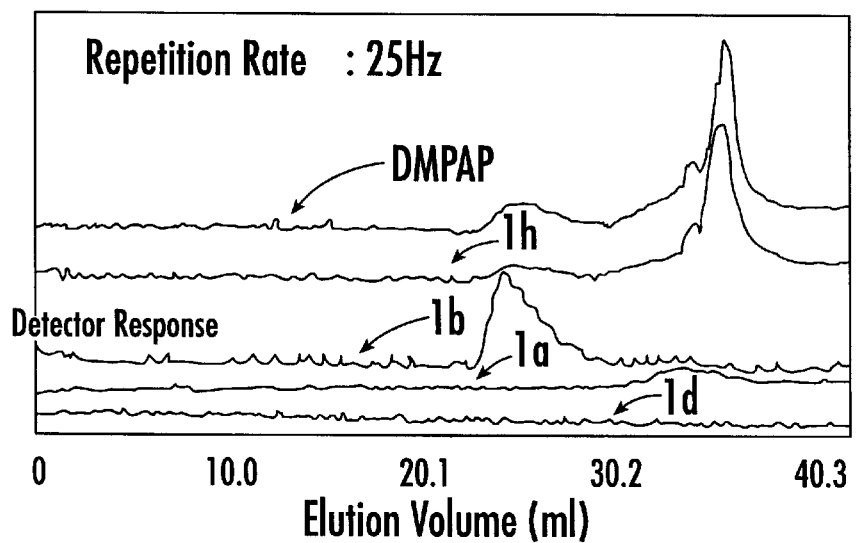
FIG. 2 is a SEC produced from LIP of MMA using DMPAP and compounds in accordance with the invention at a repetition rate of 25 Hz.

In FIG. 2, SEC traces of poly(methyl methacrylate) formed by the LIP of methyl methacrylate using DMPAP and the four compounds of the invention, the trace corresponding to compound Ib is distinctly different from the others and indicates that polymerization is initiated by a biradical mechanism. The low molecular weight peak is absent. The trace corresponding to compound Ih is also different for the others in that the SEC chromatogram does not show any splitting of the low molecular weight peak. For compound Ia, the trace is similar to that for DMPAP, suggesting that it does not initiate polymerization by a biradical mechanism. The trace for compound Id shows that no polymer is produced.

Further studies were conducted for compound Ib. LIP using this initiator was carried out at different repetition rates and the polymer formed analyzed by SEC. The results were compared with those obtained using DMPAP as the initiator, and the results are shown in FIGS. 3 and 4. As shown in FIGS. 3 and 4, at all repetition rates studied, compound Ib does not produce any low molecular weight monomer at all. At the lowest repetition rate studied, 0.1 Hz, the propagating radicals have sufficient time for polymerization and therefore produce the maximum molecular weight, At this repetition rate, even when a conventional initiator was used, low molecular species are not produced as the propagating radicals are not intercepted prematurely. As a result, the SEC traces of compound Ib and DMPAP look similar in that the traces do not show any low molecular weight species. However, a careful evaluation of the SEC traces reveals that the peak molecular weight of the polymer obtained using compound Ib as the initiator is about 1,260,000 whereas the peak molecular weight of the polymer produced using DMPAP as the initiator is about 794,000. Both of these results, the lack of low molecular weight species as well as the generation of higher molecular weight polymer, indicate that initiator Ib initiates polymerization by a biradical mechanism.

The foregoing examples are illustrative of the present invention and are not to be construed as limiting thereof. The invention is defined by the following claims, with equivalents of the claims to be included therein.

That which is claimed is:

1. A compound useful in radiation curing of photopolymerizable compounds and capable of forming a biradical compound having at least two active sites, said compound having the formula:

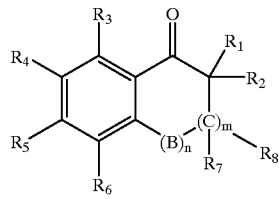

(I)

wherein:

$R_1$ and $R_2$ are each independently lower alkoxy;

$R_3$, $R_4$, $R_5$, $R_6$, $R_7$ and $R_8$ are each independently selected from the group consisting of hydrogen, lower alkoxy, lower alkyl, nitrile, aryl, and halogen;

B is C;

m is 0, 1 or 2; and n is 0 or 1.

2. The compound of claim 1, wherein:

$R_3$, $R_4$, $R_5$, $R_6$, $R_7$ and $R_8$ are each hydrogen;

m is 1; and n is 1.

3. The compound of claim 1, wherein:

$R_3$, $R_4$, $R_5$, $R_6$, $R_7$ and $R_8$ are each hydrogen;

m is 1; and n is 0.

4. The compound of claim 1, wherein:

$R_3$, $R_4$, $R_5$, $R_6$, $R_7$ and $R_8$ are each hydrogen;

m is 2; and n is 1.

5. The compound of claim 1, wherein said compound is selected from the group consisting of:

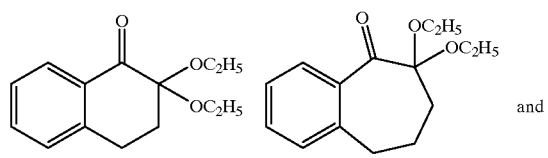

and

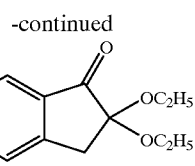

6. The compound of claim 1, wherein $R_7$ and $R_8$ are each hydrogen.

7. A photopolymerizable composition comprising a photopolymerizable compound comprising at least one ethylenically unsaturated double bond and a photoinitiator capable of forming a biradical compound having at least two active sites, wherein said photoinitiator comprises a compound having the Formula (I)

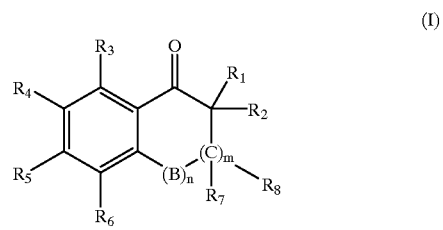

(I)

wherein:

$R_1$ and $R_2$ are each independently lower alkoxy;

$R_3$, $R_4$, $R_5$, $R_6$, and $R_8$ are each independently selected from the group consisting of hydrogen, lower alkoxy, lower alkyl, nitrile, aryl, and halogen $R_7$ is hydrogen, lower alkoxy, lower alkyl, nitrile, aryl, halogen or $R_7$ and B together with the carbon atom to which $R_7$ is attached is phenyl ring;

B is C;

m is 0, 1 or 2; and n is 0 or 1.

8. The composition of claim 7, wherein:

$R_3$, $R_4$, $R_5$, $R_6$, $R_7$ and $R_8$ each hydrogen;

m is 1; and n is 1.

9. The composition of claim 7, wherein:

$R_3$, $R_4$ $R_5$ $R_6$, R7 and $R_8$ each hydrogen;

m is 1; and n is 0.

10. The composition of claim 7, wherein:

$R_3$, $R_4$, $R_5$, $R_6$ $R_7$ and $R_8$ are each hydrogen;

m is 2; and n is 1.

11. The composition of claim 7, wherein:

$R_3$, $R_4$, $R_5$, $R_6$, $R_7$ and $R_8$ are each hydrogen;

m is 1;

n is 1; and $R_7$ and Biorether with tile carbon atom to which $R_7$ is attached is phenyl.

12. The composition of claim 7, wherein $R_7$ and $R_8$ are each hydrogen.

13. A method of polymerizing a polymerizable compound comprising at least one ethylenically unsaturated double bond, comprising exposing said compound to radiation in the presence of a photoinitiator capable of forming a biradical compound having at least two active sites, wherein said photoinitiator comprises a compound having the Formula (I)

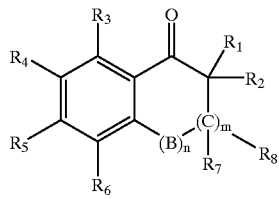
(I)

wherein:
R₁ and R₂ are each independently lower alkoxy;
R₃, R₄, R₅, R₆, and R₈ are each independently selected from the group consisting of hydrogen, lower alkoxy, lower alkyl, nitrile, aryl, and halogen R₇ is hydrogen, lower alkoxy, lower alkyl, nitrile, aryl, halogen or R₇ and B together with the carbon atom to which R₇ is attached is a phenyl ring;
B is C;
m is 0, 1 or 2; and
n is 0 or 1.

14. The method of claim 13, wherein:
m is 1; and
n is 1.

15. The method of claim 13, wherein:
R₃, R₄, R₅, R₆, R₇ and R₈ are each hydrogen;
m is 1; and
n is 0.

16. The method of claim 13, wherein:
R₃, R₄, R₅, R₆, R₇ and R₈ are each hydrogen;
m is 2; and
n is 1.

17. The method of claim 13, wherein:
R₃, R₄, R₅, R₆, R₇ and R₈ are each hydrogen;
m is 1;
n is 1, and
R₇ and B together with the carbon atom to which R₇ is attached is phenyl.

18. The method of claim 13, wherein R₇ and R₈ are each hydrogen.

19. A photopolymerizable composition comprising a photopolymerizable compound comprising at least one ethylenically unsaturated double bond and a photoinitiator capable of forming a biradical compound having at least two active sites, wherein said photoinitiator is selected from the group consisting of:

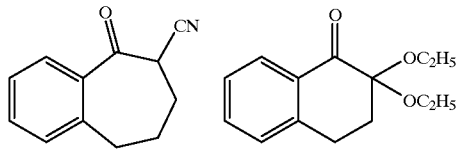

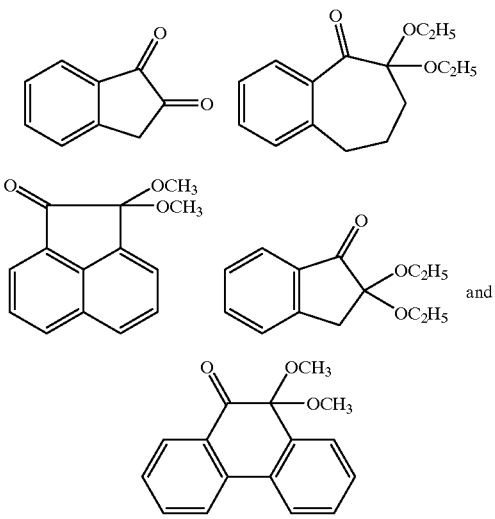

20. A method of polymerizing a polymerizable compound comprising at least one ethylenically unsaturated double bond, comprising exposing said compound to radiation in the presence of a photoinitiator capable of forming a biradical compound having at least two active sites, wherein said photoinitiator is selected from the group consisting of:

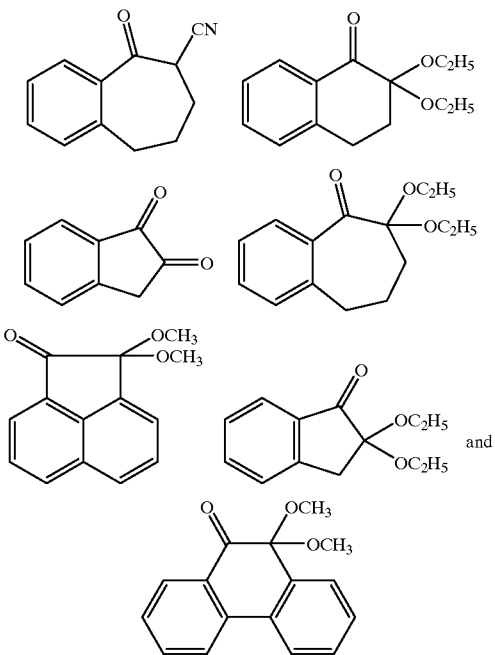

* * * * *

UNITED STATES PATENT AND TRADEMARK OFFICE
CERTIFICATE OF CORRECTION

PATENT NO. : 6,287,749 B1
DATED : September 11, 2001
INVENTOR(S) : Nagarajan et al.

Page 1 of 1

It is certified that error appears in the above-identified patent and that said Letters Patent is hereby corrected as shown below:

<u>Title page,</u>
Item [56], Reference Cited, OTHER PUBLICATIONS,
Line 2, "Tsonetsugu" should read -- Tsunetsugu --;
Line 4, "Tettahedron" should read -- Tetrahedron --.

<u>Column 12,</u>
Line 9, "arc" should read -- are --;
Line 32, after "halogen" insert a comma (,);
Line 35, after "is" insert -- a --;
Line 41, after "$R_8$" insert -- are --;
Line 46, "R7" should read -- $R_7$ --; after "$R_8$" insert -- are --;
Line 58, "Biorether" should read -- B together --; "tile" should read -- the --.

Signed and Sealed this

Twelfth Day of March, 2002

Attest:

Attesting Officer

JAMES E. ROGAN
Director of the United States Patent and Trademark Office